United States Patent
Avery et al.

(10) Patent No.: US 9,844,630 B2
(45) Date of Patent: Dec. 19, 2017

(54) CODED DRUG RESERVOIR CONNECTION ELEMENT WITH HINGED FLANGE

(75) Inventors: Richard James Vincent Avery, Gloucestershire (GB); Aled Meredydd James, Dorridge (GB)

(73) Assignee: Sanofi-Aventis Deutschland GmbH, Franfurt am Main (DE)

( * ) Notice: Subject to any disclaimer, the term of this patent is extended or adjusted under 35 U.S.C. 154(b) by 567 days.

(21) Appl. No.: 13/639,398

(22) PCT Filed: Apr. 7, 2011

(86) PCT No.: PCT/EP2011/055395
§ 371 (c)(1),
(2), (4) Date: Jan. 18, 2013

(87) PCT Pub. No.: WO2011/124632
PCT Pub. Date: Oct. 13, 2011

(65) Prior Publication Data
US 2013/0253432 A1    Sep. 26, 2013

Related U.S. Application Data (60) Provisional application No. 61/322,707, filed on Apr. 9, 2010.

(30) Foreign Application Priority Data

Jul. 29, 2010   (EP) ..................... 10171160

(51) Int. Cl.
*A61M 5/00*   (2006.01)
*A61M 5/31*   (2006.01)
(Continued)

(52) U.S. Cl.
CPC ................. *A61M 5/31* (2013.01); *A61J 1/16* (2013.01); *A61M 5/24* (2013.01); *A61M 5/5086* (2013.01);
(Continued)

(58) Field of Classification Search
CPC   A61M 5/24; A61M 5/28; A61M 5/31; A61M 5/5086; A61M 2005/244;
(Continued)

(56) References Cited

U.S. PATENT DOCUMENTS 4,614,267 A    9/1986  Larkin
5,067,948 A *  11/1991 Haber et al. .................. 604/213
(Continued)

FOREIGN PATENT DOCUMENTS

EP    1034772        9/2000
EP    1930038 A2     6/2008
(Continued)

OTHER PUBLICATIONS

International Preliminary Report on Patentability for Int. App. No. PCT/EP2011/055395, dated Oct. 18, 2012.
(Continued)

*Primary Examiner* — Kevin C Sirmons
*Assistant Examiner* — Tiffany Legette-Thompson
(74) *Attorney, Agent, or Firm* — McDonnell Boehnen Hulbert & Berghoff LLP (57) ABSTRACT

A locking mechanism is provided for use with a reservoir and a reservoir holder so as to prevent unwanted tampering with the reservoir. The mechanism comprises a main body with an aperture that is coupled to the reservoir. A hinged flange is provided on the main body. The flange folds inwards at the pivot point provided by the hinge, toward the aperture of the main body, allowing the mechanism to pass over the ferrule of the reservoir. Once the mechanism is placed over the cartridge, the flange folds toward the reservoir at the pivot point, flexing away from the main body. The flange rests against the underside of the reservoir ferrule, thereby retaining the reservoir within the locking mecha- (Continued)

nism. The locking mechanism may be for use with either a disposable or a reusable delivery device.

27 Claims, 6 Drawing Sheets

(51) Int. Cl.
| | |
|---|---|
| *A61M 5/24* | (2006.01) |
| *A61M 5/50* | (2006.01) |
| *A61J 1/16* | (2006.01) |
| *A61J 1/14* | (2006.01) |
| *A61M 5/34* | (2006.01) |

(52) U.S. Cl.
CPC .......... *A61J 1/1406* (2013.01); *A61J 2205/40* (2013.01); *A61M 5/347* (2013.01); *A61M 5/348* (2013.01); *A61M 2005/244* (2013.01); *A61M 2005/2407* (2013.01); *A61M 2205/276* (2013.01); *A61M 2205/6045* (2013.01); *Y10T 29/49826* (2015.01)

(58) Field of Classification Search
CPC .. A61M 2005/2403; A61M 2005/2407; A61M 2005/2481; A61M 2005/2485; A61M 2005/2492; A61M 2205/276; A61M 1/1406; A61M 1/1412; A61M 1/1437; A61M 1/1475; A61M 1/1481; A61M 5/348; A61M 5/347; A61M 2205/244; A61M 2205/6045; A61J 1/16; A61J 1/1406
USPC ........ 604/110, 187–188, 192, 195–198, 200, 604/211, 218, 232, 240–242, 244
See application file for complete search history.

(56) References Cited

U.S. PATENT DOCUMENTS

| | | | |
|---|---|---|---|
| 5,332,399 A * | 7/1994 | Grabenkort | ........... A61J 1/2089 604/403 |
| 5,554,134 A | 9/1996 | Bonnichsen | |
| 6,312,413 B1 * | 11/2001 | Jensen et al. | ................. 604/232 |
| 2003/0004466 A1 | 1/2003 | Bitdinger et al. | |
| 2003/0078195 A1 * | 4/2003 | Kristensen et al. | .............. 514/3 |
| 2003/0153895 A1 | 8/2003 | Leinsing | |
| 2008/0171994 A1 * | 7/2008 | Williams et al. | ............. 604/187 |

FOREIGN PATENT DOCUMENTS

| | | | |
|---|---|---|---|
| FR | EP 1034772 A1 * | 9/2000 | ........... A61J 1/2089 |
| WO | 03/047667 | 6/2003 | |
| WO | 2008/071804 | 6/2008 | |

OTHER PUBLICATIONS

Extended European Search Report issued in European Patent Application No. 10171160.4 dated Feb. 1, 2011.
Form PCT/ISA/220, Notification of Transmittal of the International Search Report and the Written Opinion of the International Searching Authority, or the Declaration dated Jun. 18, 2011.
Third Office Action issued in Chinese Patent Application No. 201180026431.x dated Mar. 24, 2015.
International Search Report for Int. App. No. PCT/EP2011/055395, dated Jul. 8, 2011.

* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
        35
```

CODED DRUG RESERVOIR CONNECTION ELEMENT WITH HINGED FLANGE

CROSS REFERENCE TO RELATED APPLICATIONS

The present application is a U.S. National Phase Application pursuant to 35 U.S.C. §371 of International Application No. PCT/EP2011/055395 filed Apr. 7, 2011, which claims priority to U.S. Provisional Patent Application No. 61/322,707 filed Apr. 9, 2010 and European Patent Application No. 10171160.4 filed Jul. 29, 2010. The entire disclosure contents of these applications are herewith incorporated by reference into the present application.

FIELD OF INVENTION

The present disclosure is generally directed to reservoirs, particularly reservoirs containing a medicament. Such medicament reservoirs may comprise an ampoule, a cartridge, a vial, or a pouch, and may be used with a medical delivery device. Exemplary medical delivery devices include, but are not limited to pen type injection devices, syringes, pen type injection syringes, pumps, inhalers, or other similar injection or infusing devices that require at least one reservoir containing at least one medicament. The medicament reservoirs may be secured to reservoir holders within the medical delivery devices. The present disclosure is particularly directed to a locking mechanism for use with a reservoir and a reservoir holder so as to prevent unwanted reservoir tampering and reservoir cross use.

BACKGROUND

Medicament reservoirs such as ampoules, cartridges, cartridge assemblies, or vials are generally known. Such reservoirs may be especially used for medicaments that may be self administered by a patient.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH$_2$ may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

For example, with respect to insulin, a patient suffering from diabetes may require a certain amount of insulin to either be injected via a pen type injection device like a pen type injection syringe or infused via a pump. With respect to certain known reusable pen type drug or medication delivery devices, a patient loads a reservoir, for example a cartridge containing a drug, for example insulin, into a proximal end of a reservoir holder, for example a cartridge holder. After the cartridge has been correctly loaded, the user may then select a dose of a medicament or may be called upon to select a dose of medicament. The dose selected by the user may be a fixed or variable dose. Accordingly, the delivery device may be a fixed dose or variable dose device. Concerning a variable dose and a respective device, the user may vary the amount of medicament being expelled out of the device. Moreover, the reservoir or cartridge may contain one dose only or multiple doses. Preferably, multiple doses may be dosed from the cartridge. Most suppliers of such cartridges recommend that the user dispose of the empty cartridges properly. Where the drug delivery device comprises a disposable device, once the cartridge is empty, the user is recommended to dispose of the entire device.

Where the drug delivery device comprises a reusable device, once the cartridge is empty or the medication contained therein has exceeded its date of expiry, the cartridge holder may be disconnected from the drug delivery device and the empty or expired cartridge may be removed and replaced with a new cartridge.

Such known self administration systems requiring the removal and reloading of empty or expired cartridges may have certain limitations. For example, in certain generally known reusable systems, a user may simply load a new cartridge into the delivery system without the drug delivery device or without the cartridge having any mechanism of preventing removal and subsequent cross use of an incorrect cartridge such that the problem could arise that the user applies the wrong cartridge and consequently the wrong medicament. Identifying an incorrect medicament is quite important, since the administration of a potentially incorrect dose of a medicament such as a short acting insulin in lieu of a long insulin could result in injury or even death. Alternatively, certain known drug delivery devices may not present a mechanism for determining if the correct type of medicament within the cartridge should be used with that particular drug delivery system. Hence, the problem could arise that a correct type of medicament is used but in the wrong type of device which is not designed to be used with this type of medicament. This potential problem could be exacerbated given that certain elderly patients, such as those suffering from diabetes, may have limited manual dexterity such that these patients possibly are not aware of using a wrong type of cartridge with their device.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be cartridges supplied by a number of different suppliers and containing a variety of different medicaments but which may fit to a single drug delivery device. This may enforce the problem of unintended cross use of different and possibly wrong medicaments or unintended cross use of types of medicaments with the wrong type of delivery device. As just one example, a first cartridge containing a first medicament from a first supplier may fit to a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

The general problem to be solved by this disclosure is to provide a locking mechanism, a corresponding drug delivery device as well as a method for securing a locking mechanism to a reservoir such that security against unintended use of a drug in connection with a respective delivery device may be improved.

SUMMARY

According to an exemplary arrangement, a locking mechanism for attaching a reservoir within a reservoir holder is provided. The locking mechanism may comprise a main body with a proximal end and a distal end, an aperture and an inner surface. The main body may be coupled to the reservoir. At least one flange may be provided on the main body. The flange may comprise a hinge, and at least a portion of the flange may retain the locking mechanism on said reservoir. Thereby, the reservoir may be locked to or within the locking mechanism. Moreover, at least one portion of the flange may retain the reservoir within the reservoir holder.

In a specific embodiment a locking mechanism for attaching a reservoir to a reservoir holder is disclosed, said mechanism comprising: a main body configured to be coupled to the reservoir, the main body comprising a proximal end and a distal end, and at least one flange provided on the main body, the flange comprising a hinge and configured such that at least a portion of the flange is folded on the hinge and retains the locking mechanism on the reservoir when the locking mechanism is coupled to the reservoir. Thereby, a reservoir may be provided being coupled to the locking mechanism to designate the reservoir for intended use only. With the aid of the locking mechanism, the reservoir may unambiguously be marked such that a user may couple the reservoir and locking mechanism to a suitable and predetermined reservoir holder only. The reservoir holder may be used within a drug delivery device. Unintended use of a wrong drug or use of a wrong type of drug with respect to the delivery device may be prevented.

According to one embodiment, the flange is configured such that at least a portion of the flange is enabled to abut against an underside of a neck part of the coupled reservoir. Several types of reservoirs may have neck parts, for example ferrules that may comprise, e.g., a pierceable seal across the open distal end of the ferrule which may be pierced by a needle assembly for delivering medication into an injection site. The main body of the locking mechanism may comprise an aperture and may be mounted via its aperture on the reservoir, especially may be pushed over the neck part of the reservoir. With this configuration of the locking mechanism, reservoirs with a neck part thereon may be used to affix, retain and lock the locking mechanism to the reservoir. Hence, common types of reservoirs may have not to be adapted to the locking mechanism.

According to a detailed embodiment, the flange is configured to fold on the hinge into an aperture toward an inner surface of the main body when said locking mechanism is mounted on said reservoir.

The locking mechanism may be pushed with its aperture over the neck part of the reservoir, whereby the folded flange may constitute a retaining means, especially a kind of snap-fit, which may come into engagement with the underside of the neck part when the locking mechanism is completely positioned on the reservoir. The flange may be folded before coupling the locking mechanism with the reservoir. But it is also conceivable that the flange is still unfolded, for example pointing in a proximal direction, while the locking mechanism is fitted axially over the reservoir. Folding of the flange may then be executed during fitting the flange over the reservoir, either as a separate operation or automatically, e.g. due to contact with a shoulder of a barrel of the reservoir.

The hinge may be a so called living hinge. The living hinge may comprise a reduced thickness of material compared to the main body. This may be cost-effective.

According to a detailed embodiment, the locking mechanism comprises first retaining means configured to secure the locking mechanism to the reservoir holder. As an example, the first retaining means comprise a ledge extending from the main body which is configured to interact with the reservoir holder. For example the ledge may mate with a groove in the reservoir holder. Alternative retention features are also possible and may comprise an interference fit, a snap fit, or a bayonet-style feature.

The locking mechanism may be designed such that it comprises a first coding feature designed to code the locking mechanism such that only retainment of the locking mechanism to a corresponding reservoir holder is enabled. Hence, the reservoir to which the locking mechanism is coupled may be coded via the locking mechanism. Coding in this context means that the locking mechanism may only be secured to a correct reservoir holder. The coding feature may provide a characteristic shape which may only fit with a corresponding shape of a reservoir holder according to a key-lock mechanism. The first coding feature may be part of the first retaining means or the first retaining means as a whole may provide coding functionalities. With the first coding feature, the locking mechanism and the coupled reservoir may be secured to the correct delivery device only. This may prevent unintended insertion of a medicament in the wrong delivery device.

According to one embodiment, the at least one flange extends along at least a portion of the perimeter of said main body. The flange may comprise a single flange or two or more flanges extending along the perimeter of the proximal end of said main body.

In another embodiment, the flange comprises a plurality of perforations. The plurality of perforations may weaken the flange, reducing the force required to fold the flange, for example in towards the inner aperture of the locking mechanism. The plurality of perforations may be present near an edge of the flange, rendering the strength of the flange weaker near the edge. Alternatively, the plurality of perforations may be present closer to the end of the flange which is directly adjacent to the main body, i.e. the base of the flange, rendering the strength of the flange weaker near the base. The dimension and shape of the perforations may be adapted to any demand. If the locking mechanism is forcibly removed from the reservoir, the flange may be damaged and may no longer be able to retain the locking mechanism to the reservoir. This may provide for a tamper-evident mechanism. Other tamper-evident features may also be envisioned, such as a label that may be affixed to the locking mechanism, that, if manipulated, may tear or rip.

According to one embodiment, the locking mechanism comprises a thread configured for receiving a threaded needle assembly, e.g. a needle hub. The thread may for example be designed on an outer surface of the main body of the locking mechanism. With this configuration, a needle assembly may be pierced into a septum of a neck part of a reservoir which is secured to the locking mechanism. Concurrently, the needle assembly may be fixed to the locking mechanism via the thread. Thus, a stable injection assembly may be provided.

In an alternative arrangement, a delivery system comprises a drug delivery device, wherein the device may comprise a dose setting mechanism. A cartridge or reservoir holder may be secured to the dose setting mechanism. A cartridge or reservoir may be contained within the reservoir holder and a locking mechanism may affix to the reservoir. The locking mechanism may comprise at least one flange. The flange may be attached to the locking mechanism at a base of said flange. The flange may comprise a living hinge near said base. At least a portion of the flange may rotate at a pivot point provided by the living hinge.

In a specific embodiment, a drug delivery system with a drug delivery device is disclosed comprising a reservoir holder, a reservoir contained within the reservoir holder, and a locking mechanism as disclosed above wherein the locking mechanism is secured, preferably locked, to the reservoir and to the reservoir holder. The drug delivery device provides a locking mechanism of the type explained above. This may enable a user for a secure and unambiguous use of a correct medicament contained within a reservoir, as the reservoir is secured to the locking mechanism which marks the reservoir to be suitable for the drug delivery device and prevents from tampering and cross use. Further security may be given by the locking mechanism since the locking mechanism only matches with the reservoir holder of the correct device such that only a reservoir of the correct type is used within the drug delivery device.

The locking mechanism may comprise a main body with an aperture extending through the center of said main body. The locking mechanism may comprise a living hinge which may comprise a reduced thickness of material compared to the main body. Moreover, at least a portion of the flange of the locking mechanism may retain said locking mechanism, for example by abutting against an underside of a ferrule on said cartridge. The flange may be folded on the hinge as explained above, thereby retaining and securing the locking mechanism to the reservoir. For example, the flange is folded inwards into the aperture of the main body of the locking mechanism, at least a part of the flange engaging with or abutting against the underside of the neck part, for example the ferrule, of the reservoir to secure the locking mechanism to the reservoir.

According to one embodiment, the reservoir holder comprises second retaining means interacting with the locking mechanism to removably secure the locking mechanism to the reservoir holder. The second retaining means may interact with first retaining means of the locking mechanism as explained above. The second retaining means may be a groove with any suitable form and shape. The reservoir holder may be designed such that it comprises a second coding feature designed to code the reservoir holder such that only interaction with a corresponding locking mechanism is enabled. The second coding feature may be part of the second retaining means or the second retaining means as a whole may provide coding functionalities. Hence, the locking mechanism may be coded to the reservoir holder. Thus, only a suitable locking mechanism containing a reservoir with a correct medicament may match with the device.

In a further aspect, there is provided a method for securing a locking mechanism according to the type explained above to a reservoir, comprising pushing the locking mechanism with its main body over a part of the reservoir, for example a neck part, wherein at least a portion of the flange of the locking mechanism is folded on the hinge such that the flange comes into engagement with the part of the reservoir, thereby securing the locking mechanism to the reservoir. According to this method, a reservoir may be preassembled with a locking mechanism to provide a prepared reservoir assembly for secure use with a suitable drug delivery device.

The scope of the invention is defined by the content of the claims. The invention is not limited to specific embodiments but comprises any combination of elements of different embodiments. Moreover, the invention comprises any combination of claims and any combination of features disclosed by the claims.

The mentioned and other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
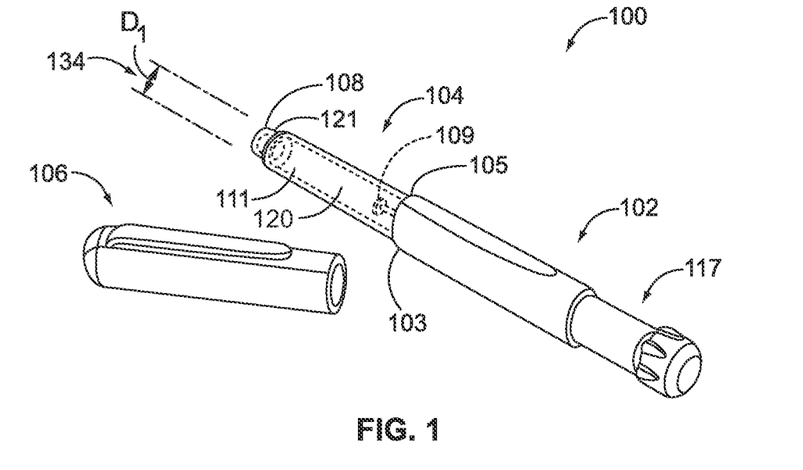
FIG. 1 illustrates an exemplary pen type drug delivery device.

Referring to FIG. 1, there is shown a drug delivery device 100 in the form of a pen type injection device, i.e. a pen type syringe. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The drug delivery device 100 may comprise a re-usable or a disposable pen type device. Where the device 100 comprises a reusable device, the cartridge holder 104 and the dose setting mechanism 102 are removably coupled together. In a disposable device, they may be permanently coupled together. In FIG. 1, the dose setting mechanism 102 may comprise a piston rod 109. The piston rod 109 may be a threaded piston rod that rotates when a dose is injected. In particular, the threaded piston rod 109 is helically moved in distal direction of the device 100 for expelling a predetermined amount of a medication out of the cartridge 120.

The dose setting mechanism 102 comprises a dose setter 117 at the proximal end of the dose setting mechanism 102. In one preferred arrangement, the dose setter 117 is rotated to set and/or deliver a dose.

To inject a previously set dose, a double ended needle assembly may be attached to a distal end 108 of the cartridge 120. Preferably, the distal end of the cartridge holder 104 comprises a thread 121 (or other suitable connecting mechanism such as a snap lock, snap fit, form fit, or bayonet lock mechanism) so that the needle assembly may be removably attached to the distal end of the cartridge holder 104. When the drug delivery device 100 is not in use, the removable cap 106 can be releasably retained over the cartridge holder 104. An inner cartridge cavity 111 defined by the cartridge holder 104 is dimensioned and configured to securely receive and retain the cartridge 120.

Figure 2:
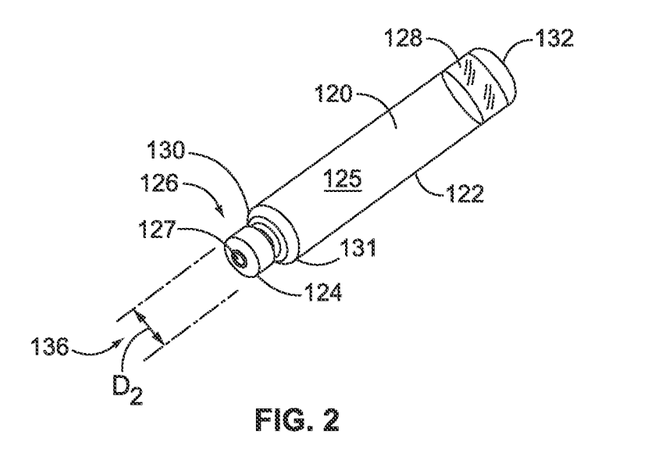
FIG. 2 illustrates a cartridge that may be loaded into a cartridge holder of the pen type drug delivery device illustrated in FIG. 1.

FIG. 2 illustrates a perspective view of the cartridge 120 that may be used with the drug delivery device 100 illustrated in FIG. 1. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck projects distally from the shoulder 131 of the barrel 122. Preferably, this smaller diameter neck 126 is provided with a large diameter annular bead (not shown) and this bead extends circumferentially thereabout at the extreme distal end of the neck 126. A pierceable seal 127 or septum is securely mounted across the open distal end defined by the neck. The seal 127 may be held in place by a metallic sleeve or ferrule 124. This ferrule 124 may be crimped around the circumferential bead at the distal end of the neck 126. The diameter of ferrule 124 is shown by $D_2$ 136. The medicament 125 is pre-filled into the cartridge 120 and is retained within the cartridge 120, in part, by the pierceable seal 127, the ferrule, e.g. a metallic sleeve 124, and the stopper 128. The stopper 128 is in sliding fluid-tight engagement with the inner tubular wall of the barrel 122. Axially directed forces acting upon the stopper 128 during dose injection or dose administration urges the medication 125 from the cartridge though a double ended needle mounted onto the distal end 130 of the cartridge holder 104 and into the injection site. Such axial forces may be provided by the piston rod 109.

A portion of the cartridge holder 104 defining the cartridge holder cavity 111 is of substantially uniform diameter represented in FIG. 1 by $D_1$ 134. This diameter $D_1$ is preferably slightly greater than the diameter $D_2$ of the cartridge 120. The interior of the cartridge holder 104 may include an inwardly-extending annual portion or stop that may be dimensioned to prevent the cartridge 120 from moving within the cartridge holder 104. In this manner, when the cartridge 120 is loaded into the cavity 111 of the cartridge holder 104 and the cartridge holder 104 is then connected to the dose setting member or mechanism 102, the cartridge 120 will be securely held within the cartridge cavity. More particularly, the neck 126 and ferrule 124 of the cartridge 120 are inserted in a proximal to distal direction into the open proximal end of the cartridge holder 104 with the ferrule 124 eventually passing entirely into the holder 104. With the holder 104 removably coupled to the dose setting mechanism 102, the proximal end of the cartridge 120 will typically abut a stop provided by the dose setting mechanism 102.

A number of doses of a medicament 125 may be dispensed from the cartridge 120. Preferably, the cartridge 120 contains a type of medicament 125 that must be administered often, such as one or more times a day. One such medicament 125 is insulin. The stopper 128 is retained in a first end or proximal end of the cartridge 120 and receives an axial force created by the piston rod 109 of the dose setting mechanism 102.

To administer a set dose, the user attaches the needle assembly comprising a double ended needle on the distal end of the cartridge holder 104. In this manner, the needle assembly pierces the seal 127 of the cartridge 120 and is therefore in liquid communication with the medicament 125. The user pushes on the dose setter 117 to inject the set dose. The same dose setting and dose administration procedure is followed until the medicament 125 in the cartridge is expended, at which time a new cartridge may be loaded in the device. To exchange an empty cartridge, the user is called upon to remove the cartridge holder 104 from the dose setting mechanism 102.

Figure 3:
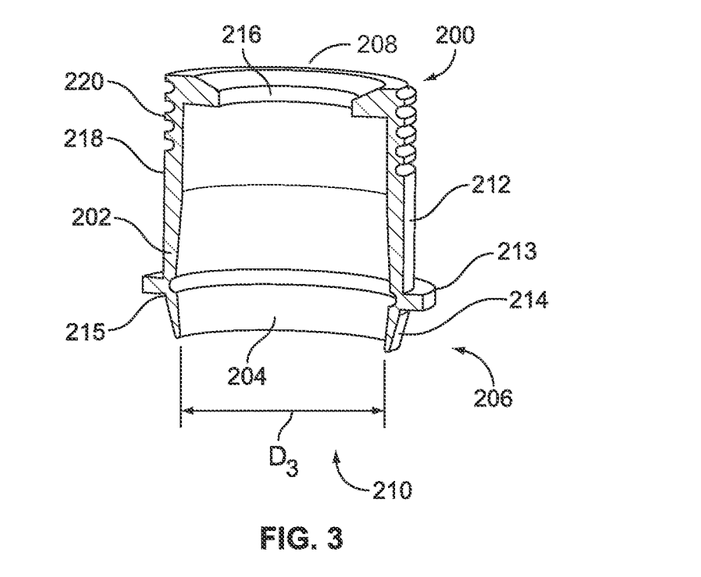
FIG. 3 illustrates a first arrangement of a locking mechanism for use with a cartridge that may be used with a pen type drug delivery device, such as the drug delivery device illustrated in FIG. 1.

FIG. 3 illustrates a cross-sectional view of a first arrangement of a locking mechanism 200 for use with a cartridge that may be used with a pen type drug delivery device 100, such as the cartridge 120 illustrated in FIG. 2. More specifically, locking mechanism 200 fits over distal end 130 of cartridge 120, and a flange 214 on locking mechanism 200 may be folded inwards on a hinge 215, creating an internal ridge that fits around ferrule 124 of the cartridge. In this manner, and as explained in greater detail below, the locking mechanism 200 can provide a locking feature to cartridge 120.

The locking mechanism 200 shown in FIG. 3 comprises a cylindrically shaped main body 202 defining a centrally located aperture 204. This aperture 204 extends from a proximal end 206 or tip to a distal end 208 of the main body 202 and, when in use, the aperture 204 is placed over the ferrule 124 located at the distal end of a cartridge. Preferably, this aperture 204 has a diameter $D_3$ 210 that is slightly larger than the diameter of the ferrule 124 of the cartridge.

The locking mechanism 200 further comprises an axially extending wall 212 that extends from flange 214 located near the proximal end of the main body 202. This axially extending wall 212 extends towards the distal end 208 of the main body 202. The axially extending wall 212 may vary, and may be as long as or longer than the cartridge when the cartridge is within the locking mechanism 200. In addition, the wall 212 may include a connector for connecting the locking mechanism 200 along with the cartridge to a dose setting mechanism 102 (i.e., the locking mechanism may become part of the cartridge holder 104). A ledge 213 may extend orthogonally from a portion of main body 202.

Near distal end 208, locking mechanism 200 is provided with a pass through 216. In one arrangement, this pass through 216 is sized or configured so that, when locking mechanism 200 is snapped over the ferrule 124 of the cartridge, pass through 216 will expose a portion of the ferrule 124 of the cartridge and will provide access to at least a portion of the pierceable seal 127 of cartridge 120. Locking mechanism 200 may be made from a flexible plastic, allowing for the part to expand over a ferrule 124 during assembly.

In one arrangement, locking mechanism 200 is intended for use with a standard double ended needle, wherein this needle comprises a hub having an internal thread 121. As such, an outer surface 218 of axial wall 212 of the main body 202 is provided with an outer thread 220 that receives such a hub of the double ended needle. Such an outer thread 220 could comprise a single or a double start outer thread 220. In addition, when such double ended needle is mounted onto the locking mechanism 200, the piercing distal needle projects through pass through 216 and into the pierceable seal 127 of the cartridge.

Figures 4, 5:
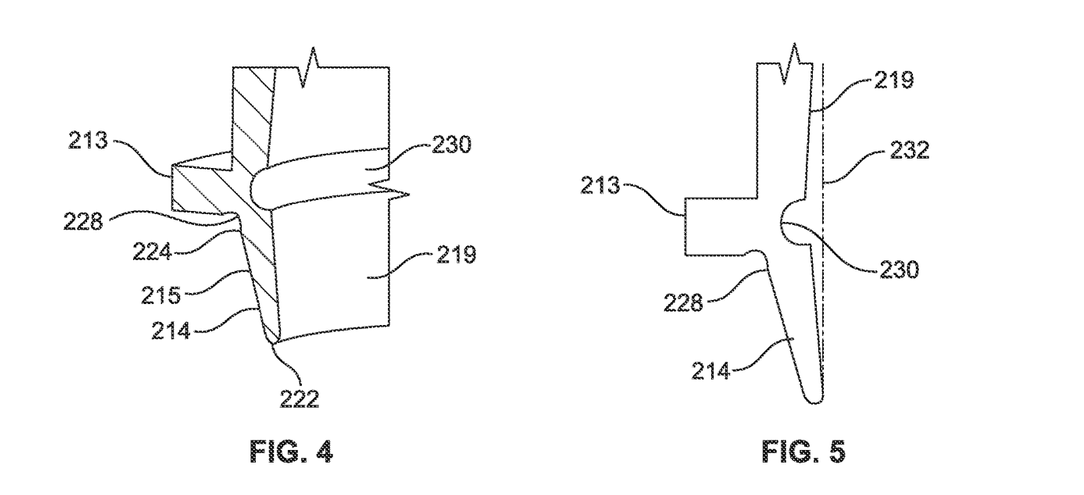
FIG. 4 illustrates an enlarged view of a portion of a locking mechanism such as the locking mechanism illustrated in FIG. 3.
FIG. 5 illustrates a profile view of a portion of a flange such as the flange shown in FIG. 4.

FIG. 4 illustrates an enlarged view of a section of flange 214. An inner surface 219 of main body 202 is shown. In this preferred arrangement, flange 214 comprises a tip or edge 222. Edge 222 comprises the proximal end of locking mechanism 200. Flange 214 also comprises a base 224 and hinge 215. In the preferred embodiment, hinge 215 is a living hinge (e.g., a flexible cross-section that allows flange 214 to hinge relative to main body 202, without significant damage to the material). Flange 214 may be made from a plastic, and may be injection molded so that hinge 215 comprises a thinned section of the plastic, to allow the hinge 215 to move and bend. Hinge 215 may comprise as part of the thinned section, an internal indentation 230 and an external indentation 228. Internal indentation 230 and external indentation 228 may vary in size and curvature to influence the point of folding of flange 214, or to control the length of the flange 214.

FIG. 5 illustrates an exemplary profile of the flange 214 of FIGS. 3 and 4. The profile of the flange 214 may be modified. For example, the thickness or the length of flange 214 may be altered to increase or decrease the locking force against the underside of the ferrule 124. Flange 214 may be tapered toward the proximal end of the flange 214, as shown in FIG. 5. Additionally, in this embodiment, the inner surface 219 of main body 202 may be angled away from an aperture diameter line 232. The space between the inner surface 219 and aperture diameter line 232 provides a recess into which the hinged flange 214 can be positioned. This may reduce or prevent the need for locking mechanism 200 to expand over the ferrule 124 during assembly. Alternatively, the flange 214 may be modified to facilitate molding, for example, by removing the recess between line 232 and inner surface 219. The locking mechanism 200 is intended for use with a cartridge holder similar to the cartridge holder 104 of FIG. 1 but somewhat modified as will be explained in greater detail below.

Figure 6:
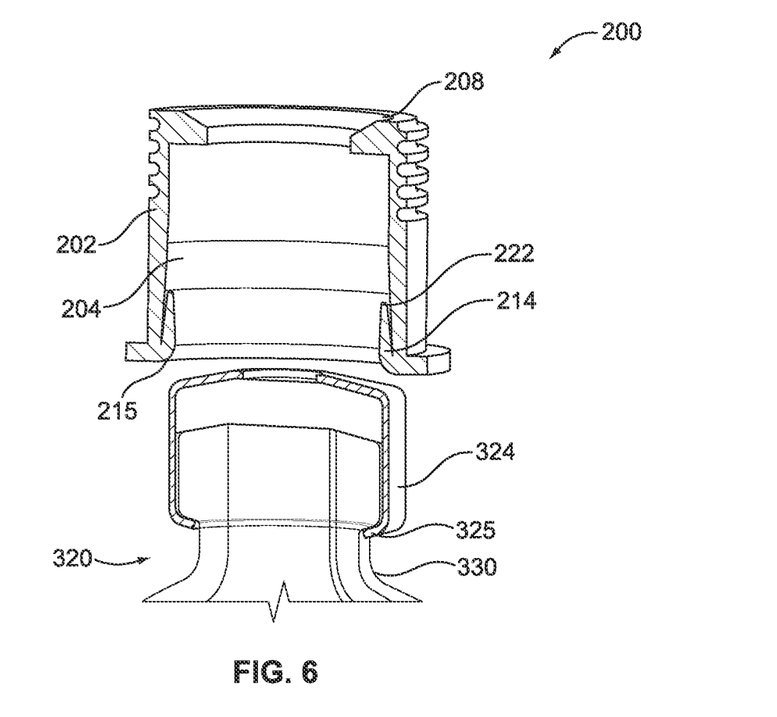
FIG. 6 illustrates a cross-sectional view of the locking mechanism of FIG. 3 before attachment to a distal cartridge portion.
Figure 7:
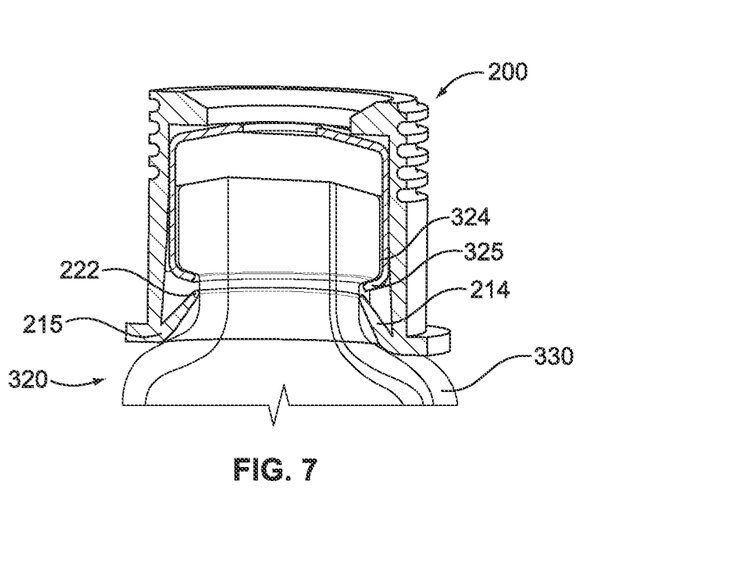
FIG. 7 illustrates a cross-sectional view of the locking mechanism of FIG. 3 attached to the distal cartridge portion.

FIGS. 6 and 7 illustrate the locking mechanism 200 or cap from FIG. 3 in one preferred method of operation. In FIG. 6, the locking mechanism 200 is preferably in a first or an assembly position. In this position, flange 214 is folded up at hinge 215 so that flange 214 is inside the aperture 204 of main body 202, the edge 222 of the flange 214 extending toward the distal end 208 of locking mechanism 200. The locking mechanism 200 is pressed or pushed down over ferrule 324 until the mechanism reaches the second position, shown in FIG. 7. Once the mechanism is pressed into the position shown in FIG. 7, edge 222 of flange 214 rotates at hinge 215, at least partially unfolding toward the cartridge. In this position, edge 222 may abut cartridge 330 and may rest below an underside 325 of ferrule 324. Other assembly sequences are also possible. For example, the flange 214 may be left unfolded and pointing in a proximal direction while the locking mechanism 200 is fitted axially over ferrule 324. Once it is past underside 325, the flange 214 may be folded inwards during the final part of axial travel, either as a separate operation or automatically due to contact with a shoulder 131 of a barrel 122 of the cartridge.

Flange 214 is operable to affix the locking mechanism 200 to a cartridge 320 in response to mechanical or tactile input from a user or as a step during an assembly process. The flange 214 is configured such that, once in the position shown in FIG. 7, when a user attempts to lift off locking mechanism 200 from cartridge 320, edge 222 will press against underside 325 of ferrule 324, preventing the removal of the mechanism. Thus, the cartridge is locked, or non-removably retained within locking mechanism 200.

Figure 8:
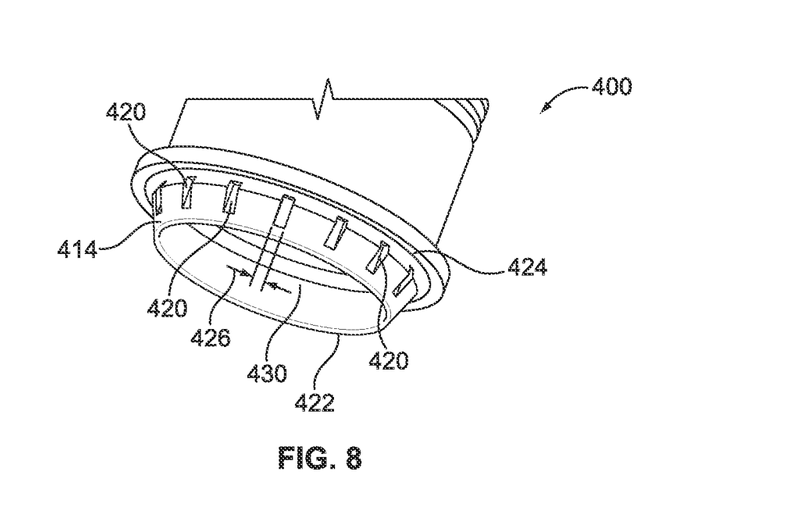
FIG. 8 illustrates an alternative arrangement of a locking mechanism.

Those of skill in the art will recognize alternative geometries for the flange 414 may also be used. For example, FIG. 8 illustrates an alternative geometry for a flange 414 on a locking mechanism 400. In FIG. 8, flange 414 comprises a plurality of perforations 420. Each perforation comprises a width 426. The plurality of perforations 420 may weaken flange 414, reducing the force required to fold flange 414 in towards an inner bore or aperture 430. The plurality of perforations 420 may be present near an edge 422 of flange 414, rendering the strength of flange 414 weaker near edge 422. Alternatively, the plurality of perforations 420 may be present closer to a base 424 of flange 414, rendering the strength of flange 414 weaker near the base. If the locking mechanism 400 is forcibly removed from the cartridge, flange 414 will be damaged and will no longer be able to retain the locking mechanism 400. This provides for a tamper-evident mechanism. Other tamper-evident features may also be envisioned, such as a label that may be affixed to the locking mechanism 400, that if manipulated, may tear or rip.

One advantage of using the locking mechanism 200 is that the fit of flange 414 against the underside of the ferrule prevents the locking mechanism 200 from unwanted removal. That is, flange 414 prevents unwanted removal of the locking mechanism 200 from the cartridge when a double ended needle is either attached or removed from the distal end of the locking mechanism 200.

Figure 9:
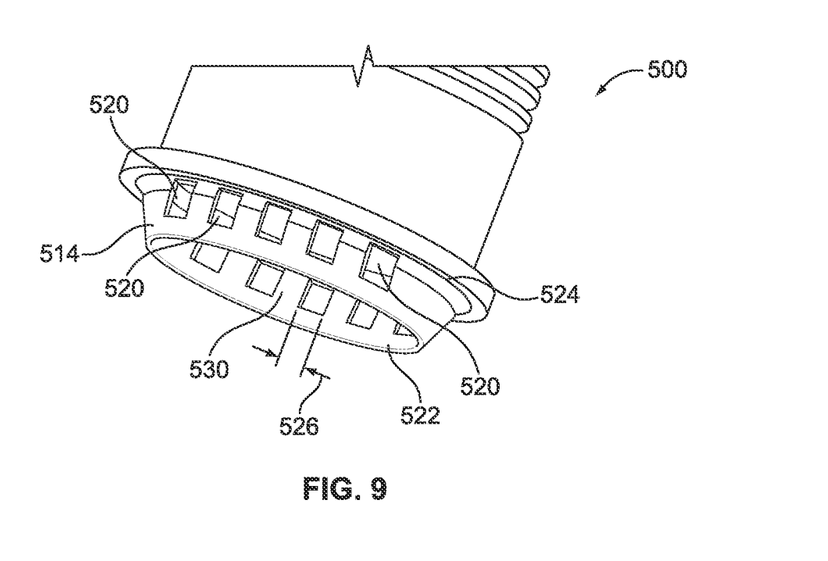
FIG. 9 illustrates an alternative arrangement of a locking mechanism.

Another alternative exemplary embodiment is shown in FIG. 9. In this alternative embodiment, a locking mechanism 500 comprises a flange 522 with plurality of perforations 520. The plurality of perforations 520 on flange 522 are cut in the radial direction, and comprise a width 526 greater than the width of the plurality of perforations 420 from FIG. 8. The perforations may not be present along the entire circumference of flange 522. The plurality of perforations 520 may weaken flange 514, reducing the force required to fold flange 514 in towards an inner bore or aperture 530.

Figure 10:
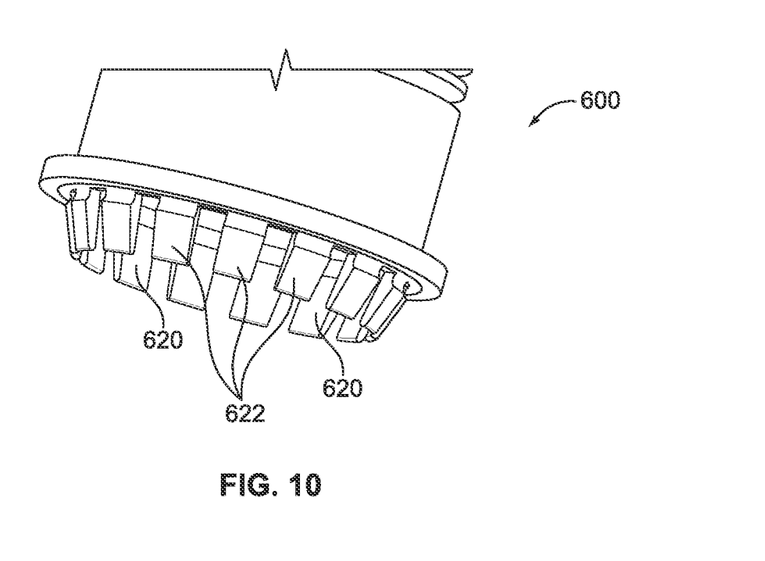
FIG. 10 illustrates an alternative arrangement of a locking mechanism.

FIG. 10 illustrates another alternative exemplary embodiment of a locking mechanism 600. In this embodiment, instead of a single flange with perforations, a plurality of flanges 622 are separated by a plurality of gaps 620. The gaps 620 may be cut or tooled out of a single flange, wherein the cut extends the entire length of flange 622, resulting in the plurality of flanges shown.

Figure 11:
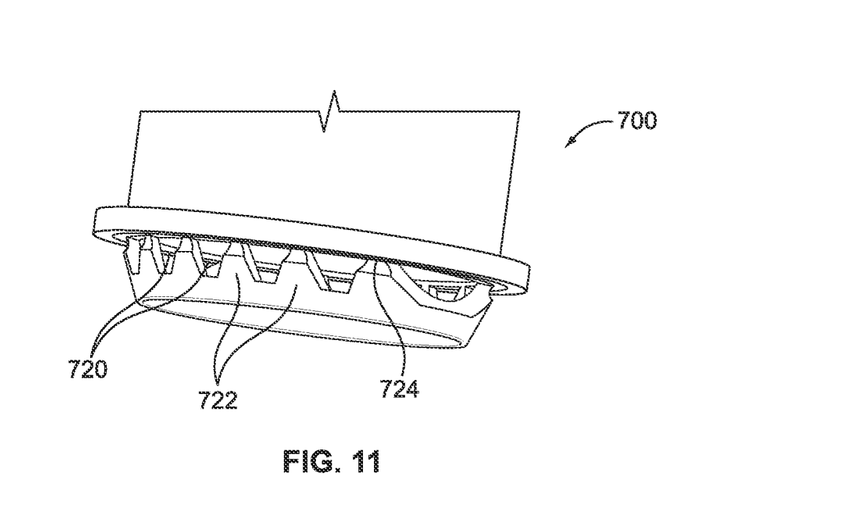
FIG. 11 illustrates an alternative arrangement of a locking mechanism.

FIG. 11 illustrates another alternative exemplary embodiment of a locking mechanism 700. In this alternative embodiment, a plurality of perforations 720 are cut on a flange 722 with angled sides, resulting in reduced flange material at a base 724 of flange 722.

Figure 12:
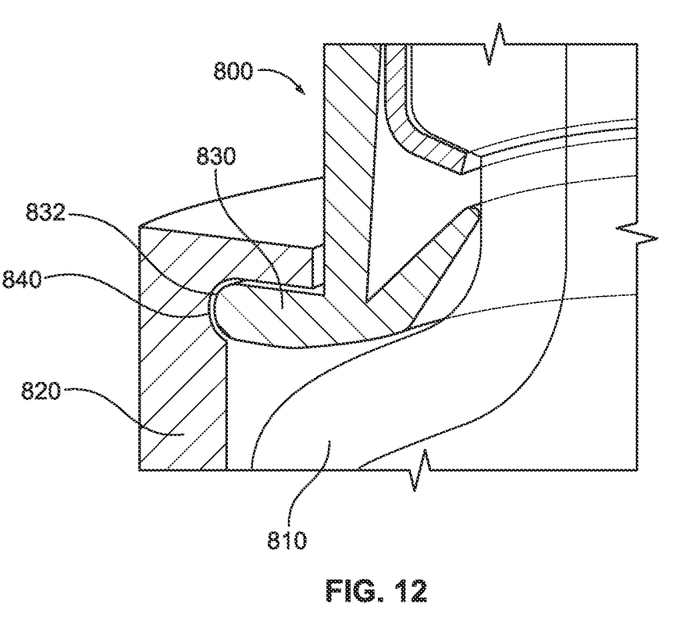
FIG. 12 illustrates an enlarged cross-sectional view of a distal cartridge portion and a distal cartridge holder portion.

FIG. 12 illustrates an enlarged cross-sectional view of a locking mechanism 800 with a distal cartridge holder portion 820 and a distal cartridge portion 810. The proximal end (not shown) of the cartridge holder 820 would include a similar releasable connection mechanism (e.g., thread, snap lock, snap fit, bayonet lock, etc.) as the cartridge holder 104 illustrated in FIG. 1. As illustrated, cartridge holder 820 has a shoulder at its distal end that overlaps with an external ledge 830 of the locking mechanism 800, and hence retains the cartridge 810 via the locking mechanism 800 in the cartridge holder 820. In this embodiment, the external ledge 830 comprises a curved edge 832. The cartridge holder 820 comprises a corresponding groove or channel 840.

The ledge 830 may fit within groove or channel 840, temporarily securing cartridge holder 810 to locking mechanism 800, such that the cartridge will not accidentally fall out of the holder, but may be easily pushed out of engagement by the user. Alternative retention features are also possible, and may comprise an interference fit, a snap fit, or a bayonet-style feature.

Locking mechanism 200, 400, 500, 600, 700, 800 may incorporate an interlocking means to prevent rotation relative to the cartridge holder. As an example, the locking mechanism 200, 400, 500, 600, 700, 800 may comprise protrusions with a triangular section pointed towards the distal end. As another example, rotation may be prevented by friction between the cap and the holder. The bendable feature may comprise a non-return element such as a rib that extends essentially orthogonally from the feature, locking the feature in place after snapping it into the second position.

The disclosed locking mechanism 200, 400, 500, 600, 700, 800 may apply to any medication delivery device 100, with any type of reservoir or primary pack, e.g. inhaler, pouch. The disclosed locking mechanism 200, 400, 500, 600, 700, 800 may also comprise a coding method to the cartridge holder to prevent insertion of a cartridge into the incorrect holder. The coding feature may be provided by any form and shape of the first and second retaining means, e.g. the ledge 213, 830 and the groove 840. The locking mechanism 200, 400, 500, 600, 700, 800 may comprise a color that distinguishes the cap to be used for a specific drug.

The disclosed locking mechanism 200, 400, 500, 600, 700, 800 results in a number of advantages. For example, the proposed locking mechanism 200 helps to ensure that a delivery device can only be used with a medicament 125 for which the device is intended. The disclosed locking mechanism 200, 400, 500, 600, 700, 800 helps to prevents a user from removing the locking mechanism 200, 400, 500, 600, 700, 800 and fastening it to another cartridge. The mechanism may also be tamper-evident. If removal is attempted, the locking mechanism 200, 400, 500, 600, 700, 800 may become damaged.

The disclosed locking mechanism 200, 400, 500, 600, 700, 800 also results in a low cost mechanism since the interface does not require a large number of parts and can be manufactured in a cost effective manner.

Exemplary embodiments of the present invention have been described. Those skilled in the art will understand, however, that changes and modifications may be made to these arrangements without departing from the true scope and spirit of the present invention, which is defined by the claims.

The invention claimed is:

1. A locking mechanism for attaching a reservoir containing a medicament to a reservoir holder of a drug delivery system, the locking mechanism comprising:
    a main body configured to be coupled to the reservoir, the main body comprising a proximal end and a distal end and defining an aperture at the proximal end, and
    at least one flange provided at the proximal end of the main body, the flange comprising a hinge and being configured to fold on the hinge, such that at least a portion of the flange is folded on the hinge into the aperture toward an inner surface of the main body and abuts against a neck of the reservoir and retains the locking mechanism on the reservoir when the locking mechanism is mounted with its aperture on the reservoir, wherein the neck of the reservoir projects distally from a shoulder part of the reservoir,
    wherein the flange is pointing in a proximal direction when the flange is unfolded, and wherein the flange is pointing in a distal direction when the flange is folded.

2. The locking mechanism of claim 1 wherein the flange is configured such that, when the flange is pointing in the distal direction, mounting the locking mechanism on the reservoir causes the flange to fold inwards on the hinge toward the neck of the reservoir due to contact of the hinge with the shoulder part of the reservoir.

3. The locking mechanism of claim 1 wherein the hinge comprises a reduced thickness of material compared to the main body.

4. The locking mechanism of claim 1 wherein the flange is configured to abut against an underside of the neck of the reservoir when the flange is folded on the hinge into the aperture.

5. The locking mechanism of claim 1 comprising a first coding feature designed to code the locking mechanism such that only retainment of the locking mechanism to a corresponding reservoir holder is enabled.

6. The locking mechanism of claim 1 wherein the at least one flange extends along at least a portion of the perimeter of the main body.

7. The locking mechanism of claim 1 wherein the locking mechanism comprises a thread configured for receiving a threaded needle hub.

8. The locking mechanism of claim 1, wherein the flange is located inward from the inner surface of the main body when the flange is folded and wherein the flange extends inwardly from the inner surface of the main body when the flange is unfolded.

9. The locking mechanism of claim 1, wherein when unfolded the flange is tapered toward a proximal end.

10. The locking mechanism of claim 1 wherein the locking mechanism further comprises a first retaining mechanism configured to secure the locking mechanism to the reservoir holder.

11. The locking mechanism of claim 10 wherein the first retaining mechanism comprises a ledge extending from the main body which is configured to interact with the reservoir holder.

12. The locking mechanism of claim 1 wherein the at least one flange comprises a plurality of perforations.

13. The locking mechanism of claim 12 wherein the plurality of perforations is positioned near an end of the flange which is directly adjacent to the main body.

14. The locking mechanism of claim 1, wherein the aperture has an aperture diameter at a proximal end of the main body and wherein the inner surface of the main body is angled away from an aperture diameter line.

15. The locking mechanism of claim 14, wherein a space between the inner surface of the main body and the aperture diameter line provides a recess, which is configured to receive the hinged flange, and
wherein the hinged flange is configured to be positioned in the recess.

16. A method for securing the locking mechanism according to claim 1 to a reservoir, comprising:
pushing the locking mechanism with its main body over the neck of the reservoir, wherein at least a portion of the flange of the locking mechanism is folded on the hinge into the aperture toward the inner surface of the main body such that the flange comes into engagement with the neck of the reservoir, thereby securing the locking mechanism to the reservoir.

17. The method of claim 16 wherein pushing the locking mechanism with its main body over the neck of the reservoir further comprises causing the hinge to contact the shoulder part of the reservoir such that the flange folds inwards on the hinge toward the neck of the reservoir due to the contact with the shoulder part.

18. A system comprising:
a drug delivery device comprising:
a reservoir holder, and
a reservoir contained within the reservoir holder; and
a locking mechanism comprising:
a main body configured to be coupled to the reservoir, the main body comprising a proximal end and a distal end and defining an aperture at the proximal end, and
at least one flange provided at the proximal end of the main body, the flange comprising a hinge and being configured to fold on the hinge, such that at least a portion of the flange is folded on the hinge into the aperture toward an inner surface of the main body and abuts against a neck of the reservoir and retains the locking mechanism on the reservoir when the locking mechanism is mounted with its aperture on the reservoir, wherein the neck of the reservoir projects distally from a shoulder part of the reservoir,
wherein the flange is pointing in a proximal direction when the flange is unfolded, and wherein the flange is pointing in a distal direction when the flange is folded,
wherein the locking mechanism is retained to the reservoir and to the reservoir holder.

19. The system of claim 18 wherein the reservoir holder comprises a second coding feature designed to code the reservoir holder such that only interaction with a corresponding locking mechanism is enabled.

20. The system of claim 18 wherein the reservoir holder is removably secured to a dose setting mechanism of the drug delivery device.

21. The system of claim 18 wherein the flange is configured to abut against an underside of the neck of the reservoir when the flange is folded on the hinge into the aperture.

22. The system of claim 18, wherein the flange is located inward from the inner surface of the main body when the flange is folded and wherein the flange extends inwardly from the inner surface of the main body when the flange is unfolded.

23. The system of claim 18, wherein when unfolded the flange is tapered toward a proximal end.

24. The system of claim 18 wherein the reservoir holder comprises a second retaining mechanism interacting with the locking mechanism to secure the locking mechanism to the reservoir holder.

25. The system of claim 24 wherein the second retaining mechanism comprises a groove in the reservoir holder.

26. The system of claim 18, wherein the aperture has an aperture diameter at a proximal end of the main body and wherein the inner surface of the main body is angled away from an aperture diameter line.

27. The system of claim 26, wherein a space between the inner surface of the main body and the aperture diameter line provides a recess, which is configured to receive the hinged flange, and
wherein the hinged flange is configured to be positioned in the recess.

* * * * *